US009149351B2

(12) United States Patent
Rane et al.

(10) Patent No.: US 9,149,351 B2
(45) Date of Patent: Oct. 6, 2015

(54) APPARATUS AND METHOD FOR REPAIRING VAGINAL RECONSTRUCTION

(75) Inventors: Ajay Rane, Townsville (AU); Malcolm I. Frazer, Benowa (AU)

(73) Assignee: AMS Research Corporation, Minnetonka, MN (US)

( * ) Notice: Subject to any disclaimer, the term of this patent is extended or adjusted under 35 U.S.C. 154(b) by 257 days.

(21) Appl. No.: 13/614,012

(22) Filed: Sep. 13, 2012

(65) Prior Publication Data

US 2013/0006050 A1   Jan. 3, 2013

Related U.S. Application Data

(62) Division of application No. 12/381,459, filed on Mar. 12, 2009, now abandoned.

(60) Provisional application No. 61/036,688, filed on Mar. 14, 2008.

(51) Int. Cl.
*A61F 2/00* (2006.01)
*A61B 17/06* (2006.01)

(52) U.S. Cl.
CPC ......... *A61F 2/0045* (2013.01); *A61B 17/06109* (2013.01); *A61B 17/06166* (2013.01)

(58) Field of Classification Search
CPC ........... A61F 2/00–2/95; A61F 2/0031; A61F 2/0036; A61F 2/0045; A61F 2/0063
USPC .......................... 600/29–31, 37; 606/139–158
See application file for complete search history.

(56) References Cited

U.S. PATENT DOCUMENTS

| 4,172,458 | A | 10/1979 | Pereyra |
| 5,922,026 | A | 7/1999 | Chin |
| 6,306,079 | B1 | 10/2001 | Trabucco |
| 6,502,578 | B2 | 1/2003 | Raz et al. |

(Continued)

FOREIGN PATENT DOCUMENTS

| DE | 19544162 | 4/1997 |
| EP | 0248544 A1 | 12/1987 |

(Continued)

OTHER PUBLICATIONS

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

(Continued)

*Primary Examiner* — Catherine B Kuhlman
(74) *Attorney, Agent, or Firm* — Kagan Binder, PLLC

(57) ABSTRACT

A system for treating vaginal prolapse including two implants, each implant including a mesh support portion and two mesh extension portions, wherein for each implant the support portion is capable of contacting vaginal sulcus tissue while the two extension portions extend to tissue of an obturator foramen. The implant may include a mesh strip, with the support portion having a length between 4 and 6 centimeters, with the total length of the mesh strip being between 15 and 20 centimeters, and with the mesh strip being of substantially uniform width in the range from 0.5 to 1.3 centimeters. The implant may include two sutures, with one suture connected at each opposing end of the implant, and/or the implant may include one or multiple sutures connected along a length of the implant.

8 Claims, 4 Drawing Sheets

(56) References Cited

U.S. PATENT DOCUMENTS

| | | | |
|---|---|---|---|
| 6,575,897 B1 | 6/2003 | Ory | |
| 6,592,515 B2 | 7/2003 | Thierfelder | |
| 7,087,065 B2 | 8/2006 | Ulmsten et al. | |
| 7,131,943 B2 | 11/2006 | Kammerer | |
| 7,131,944 B2 | 11/2006 | Jacquetin | |
| 7,175,591 B2 | 2/2007 | Kaladelfos | |
| 7,347,812 B2 | 3/2008 | Mellier | |
| 7,351,197 B2 | 4/2008 | Montpetit et al. | |
| 7,393,320 B2 | 7/2008 | Montpetit et al. | |
| 7,407,480 B2 | 8/2008 | Staskin | |
| 7,494,495 B2 | 2/2009 | Delorme et al. | |
| 7,500,945 B2 | 3/2009 | Cox | |
| 7,517,313 B2 | 4/2009 | Thierfelder et al. | |
| 7,588,598 B2 | 9/2009 | Delorme et al. | |
| 7,608,036 B2 | 10/2009 | Raz et al. | |
| 7,740,576 B2 | 6/2010 | Hodroff | |
| 7,794,385 B2 | 9/2010 | Rosenblatt | |
| 2002/0028980 A1 | 3/2002 | Thierfelder et al. | |
| 2003/0176762 A1* | 9/2003 | Kammerer | 600/30 |
| 2004/0039453 A1 | 2/2004 | Anderson et al. | |
| 2004/0267088 A1 | 12/2004 | Kammerer | |
| 2005/0004427 A1 | 1/2005 | Cervigni | |
| 2005/0199249 A1 | 9/2005 | Karram | |
| 2005/0245787 A1 | 11/2005 | Cox et al. | |
| 2005/0278037 A1 | 12/2005 | Delorme et al. | |
| 2005/0283189 A1 | 12/2005 | Rosenblatt et al. | |
| 2006/0063968 A1* | 3/2006 | Anderson et al. | 600/30 |
| 2006/0122457 A1 | 6/2006 | Kovac | |
| 2006/0173237 A1 | 8/2006 | Jacquetin | |
| 2006/0195011 A1 | 8/2006 | Arnal et al. | |
| 2006/0229493 A1* | 10/2006 | Weiser et al. | 600/37 |
| 2007/0173864 A1 | 7/2007 | Chu | |

FOREIGN PATENT DOCUMENTS

| | | |
|---|---|---|
| EP | 1060714 A3 | 9/2002 |
| FR | 285217 | 10/2004 |
| IT | 1299162 | 4/1998 |
| WO | WO9916381 A1 | 4/1999 |
| WO | WO0064370 A1 | 2/2000 |
| WO | WO0027304 A1 | 5/2000 |
| WO | WO0057812 A1 | 10/2000 |
| WO | WO0106951 A1 | 2/2001 |
| WO | WO02078552 A1 | 10/2002 |
| WO | WO03003778 A1 | 4/2003 |
| WO | WO03028585 A2 | 4/2003 |
| WO | WO03047476 A1 | 6/2003 |
| WO | WO03068107 A1 | 8/2003 |
| WO | WO03073960 A1 | 9/2003 |
| WO | WO03096929 A1 | 11/2003 |
| WO | WO2004012626 A1 | 2/2004 |
| WO | WO2004045457 A1 | 6/2004 |
| WO | WO2005037132 A2 | 4/2005 |
| WO | WO2005087153 A2 | 9/2005 |
| WO | WO2005094741 A1 | 10/2005 |
| WO | WO2005112842 A1 | 12/2005 |
| WO | WO2006108145 A1 | 10/2006 |
| WO | WO2007002071 A1 | 1/2007 |
| WO | WO2007014241 A1 | 2/2007 |
| WO | WO2007016083 A1 | 2/2007 |
| WO | WO2007059199 A2 | 5/2007 |
| WO | WO2007081955 A1 | 7/2007 |
| WO | WO2007146784 A2 | 12/2007 |
| WO | WO2007149348 A2 | 12/2007 |
| WO | WO2008124056 A1 | 10/2008 |
| WO | WO2009017680 A2 | 2/2009 |

OTHER PUBLICATIONS

Burch, John C., Urethrovaginal Fixation to Cooper'S Ligament for Correction of Stress Incontinence, Cystocele, and Prolapse, Am. J. Obst. & Gyn, vol. 31, pp. 281-290 (1961).

Cervigni, Mauro et al., The Use of Synthetics in the Treatment of Pelvic Organ Prolapse, Voiding Dysfunction and Female Urology, vol. 11, pp. 429-435 (2001).

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Farnsworth, B.N., Posterior Intravaginal Slingplasty (Infracoccyceal Sacropexy) for Sever Posthysterectomy Vaginal Vault Prolase—A Preliminary Report on Efficacy and Safety, Int Urogynecology J, vol. 13, pp. 4-8 (2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, No. 6 (Dec. 1996).

Flood, C.G. et al., Anterior Colporrhaphy Reinforce With Marlex Mesh for the Treatment of Cystoceles, International Urogynecology Journal, vol. 9, pp. 200-204 (1998).

Guner, et al., Transvaginal Sacrospinous Colpopexy for Marked Uterovaginal and Vault Prolapse, Inter J of Gynec & Obstetrics, vol. 74, pp. 165-170 (2001).

IVS Tunneller, Australian Medical design Breakthrough for GSI, mixed incontinence and vault prolapse, AMA Medical Products, 4 pages (no date).

Julian, Thomas, The Efficacy of Marlex Mesh in the Repair of Sever, Recurrent Vaginal Prolapse of the Anterior Midvaginal Wall, Am J. Obstet Gynecol, vol. 175, n. 6, pp. 1472-1475 (Dec. 1996).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Lichtenstein, Irving L. et al, The Tension Free Hernioplasty, The American Journal of Surgery, vol. 157 pp. 188-193 (Feb. 1989).

Marchionni, Mauro et al., True Incidence of Vaginal Vault Prolapse—Thirteen Years of Experience. Journal of Reproductive Medicine, vol. 44, n. 8, pp. 67-684 (Aug. 1999).

Marinkovic, Serge Peter et al., Triple Compartment Prolaspse: Sacrocolpopexy With Anterior and Posterior Mesh Extensions, Br J Obstet Gynaecol, vol. 110, pp. 323-326 (Mar. 2003).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968).

Morley, George W. et al., Sacrospinous Ligament Fixations for Eversion of the Vagina, Am J Obstet Gyn, vol. 158, n. 4, pp. 872-881 (Apr. 1988).

Nicita, Giulio, A New Operation for Genitourinary Prolapse, Journal of Urology, vol. 160, pp. 741-745 (Sep. 1998).

Paraiso et al., Laparoscopic Surgery for Enterocele, Vaginal Apex Prolapse and Rectocele, Int. Urogynecol J, vol. 10, pp. 223-229 (1999).

Petros, Peter E. Papa et al., Pelvic Floor Rehabilitaion According to the Integrated Theory of Female Urinary Incontinence, Chapter 7, pp. 249-258 (book chapter).

Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pa.

Petros, Peter E. Papa, Vault Prolapse II; Restoration fo Dynamic Vaginal Supports by Infracoccygeal Sacropexy, An Axial Day-Case Vaginal Procedure, Int Urogynecol J, vol. 12, pp. 296-303 (2001).

Richter, K., Massive Eversion of the Vagina: Pathogenesis, Diagnosis and therapy of the "True" Prolapse of the Vaginal Stump, Clin obstet gynecol, vol. 25, pp. 897-912 (1982).

Sullivan, Eugene S. et al., Total Pelvic Mesh Repair a Ten-Year Experience, Dis. Colon Rectum, vol. 44, No. 6, pp. 857-863 (Jun. 2001).

Swift, S.E., et al., Case-Control Study of Etiologic Factors in the Development of Sever Pelvic Organ Prolapse, Int Urogynecol J, vol. 12, pp. 187-192 (2001).

(56) References Cited

OTHER PUBLICATIONS

Visco, Anthony G. et al., Vaginal Mesh Erosion After Abdominal Sacral Colpopexy, Am J Obstet Gynecol, vol. 184, n. 3, pp. 297-302.

Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).

Winters et al., Abdominal Sacral Colpopexy and Abdominal Enterocele Repair in the Management of Vaginal Vault Prolapse, Urology, vol. 56, supp. 6A, pp. 55-63 (2000).

Zacharin, Robert et al., Pulsion Enterocele: Long-Term Results of an Abdominoperineal Technique, Obstetrics & Gynecology, vol. 55 No. 2, pp. 141-148 (Feb. 1980).

Mouly, Patrick et al., Vaginal Reconstruction of a Complete Vaginal Prolapse: The Trans Obturator Repair, Journal of Urology, vol. 169, p. 183 (Apr. 2003).

Kettel, L. Michael et al., An Anatomical Evaluation of the Sacrospinous Ligament Colpopexy, Surg. Gynecol. Obstet., 168(4):318-22, Apr. 1989.

Flynn, B.J. et al., Surgical Management of the Apical Vaginal Defect, Curr. Opin. Urol. 12(4):353-58, Jul. 2002.

Buller, J.L. et al., Uterosacral Ligament: Description fo Anantomic Relationships to Optimize Sergical Safety, Obstet. Gynecol. 97:873-79, 2001.

Brochure, "GPS for Pelvic Floor Repair," Gynecare Prolift, 6 pages, 2005.

Greene, Frederick, "Repair of Rectal Prolapse Using a Puborectal Sling Procedure," Arch Surg, vol. 118, pp. 398-401 (Apr. 1983).

Shafik, Ahmed, "Puborectoplasty, New Technique for the Repair of Fecal Incontinence," Dig. Surg. 1991; 8: pp. 182-186.

McMahan et al., Rectal prolapse. An update on the Rectal sling procedure,: Am Surg., vol. 53, No. 1, pp. 37-40, 1987.

O'Rourke D, et al., "A puborectal sling in the management of anal incontinence and rectal prolapse," Aust N Z J Surg., vol. 55, No. 5, pp. 493-495, 1985.

O'Rourke D, et al., "An anorectal sling in the treament of rectal prolapse and incontinence," Aust N Z J Surg., vol. 44, No. 2, pp. 144-146, 1974.

* cited by examiner

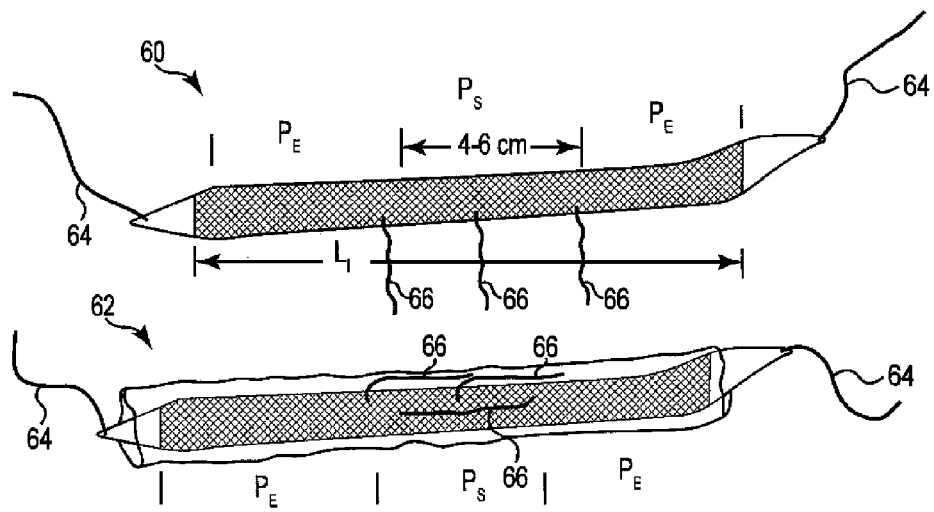
Fig. 2
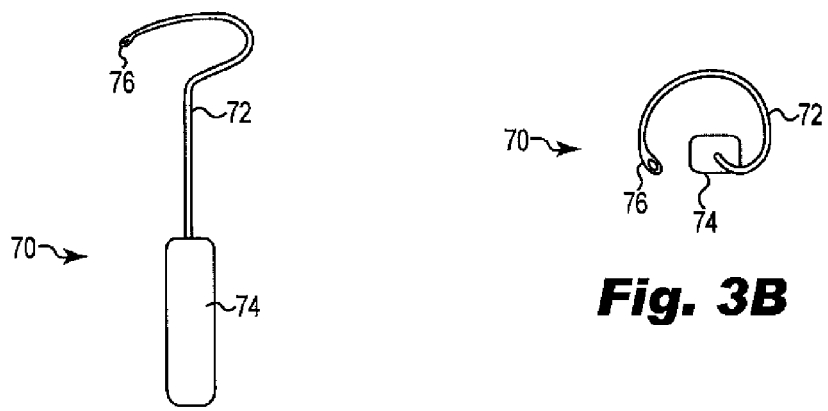
Fig. 3A  Fig. 3B

APPARATUS AND METHOD FOR REPAIRING VAGINAL RECONSTRUCTION

CROSS-REFERENCE TO RELATED APPLICATION

The present patent application is a divisional application of U.S. patent application Ser. No. 12/381,459, filed Mar. 12, 2009, which claims the benefit under 35 U.S.C. §119(e) of U.S. Provisional Patent Application No. 61/036,688, filed on Mar. 14, 2008, the entire disclosures of which are incorporated herein by reference in their entireties.

TECHNICAL FIELD

The present invention relates to vaginal prolapse repair and more particularly to transvaginal prolapse repair.

BACKGROUND

Anterior vaginal prolapse repairs have historically had recurrence rates of around thirty percent. This is because traditional surgery uses devitalized tissues and paravaginal defects are very difficult to correct transvaginally. Laparoscopic paravaginal defect correction is technically very difficult and there is no data looking at its efficacy. The use of "mesh" for prolapse repair shows greater efficacy in a randomized trial by Sand et al. but does not address total anterior vaginal reconstruction and certainly not paravaginal defect correction.

SUMMARY

The invention relates to treatments of vaginal prolapse of the types referred to as anterior vaginal prolapse, cystocele, lateral defects, and paravaginal defects. According to embodiments of the invention, mesh implants are provided and placed in a pelvic region to support vaginal tissue, bladder tissue, or both, either directly or by supporting tissue that would otherwise support the bladder or vaginal tissue.

A paravaginal defect is a defect of tissue that supports the bladder in a position superior to the vagina. This type of defect can cause the bladder to fall into the vagina and result in vaginal prolapse, including anterior vaginal prolapse such as cystocele, or a lateral defect. An example of a paravaginal defect is a defect in the hammock-type tissue (e.g., pubocervical fascia) that supports the bladder, such as a tear or detachment of the tissue at a "tree end" of the tissue (e.g., the portion of the fascia away from the vaginal tissue, near the arcus tendineus) rather than a tear in the sheet (midline defect). A specific example of a paravaginal defect can be torn pubocervical fascia along or near an arcus tendineus. The defect may be unilateral or bilateral, either way resulting in a cystocoele. A lateral defect (e.g., paravaginal defect) can allow bladder tissue to become unsupported and contact vaginal tissue, resulting in vaginal prolapse, e.g., anterior vaginal prolapse or cystocele. Implants and methods of the present description can treat such conditions by supporting or replacing one or more of vaginal tissue, bladder tissue, or vaginal support tissue or bladder support tissue (e.g., pubocervical fascia).

As used herein, the vaginal sulcus is the lateral depth of vagina in the anterior compartment. The vaginal sulcus is usually between 2 and 5 centimeters deep and increases in depth as the vagina extends in a posterior direction.

Advantages of the present invention include reconstructing the arcus tendineus with prolene, thereby giving strength. Another advantage includes providing more anatomical repair. The procedure is a minimally invasive technique when compared with abdominal paravaginal repair.

In one aspect, the invention relates to an implantable device useful for treating vaginal prolapse including a paravaginal defect. The device includes a mesh support portion and multiple mesh extension portions, the support portion is capable of supporting a bladder. Each extension portion is capable of extending to tissue of an obturator foramen while the support portion supports the bladder.

In another aspect, the invention relates to a system for treating vaginal prolapse. The system includes two implants. Each implant includes a mesh support portion and two mesh extension portions. For each implant the support portion is capable of contacting vaginal sulcus tissue while the two extension portions extend to tissue of an obturator foramen.

In another aspect, the invention relates to a method of treating cystocele related to a lateral vaginal defect. The method includes: providing an implant as described herein; making an upper vaginal midline incision; passing the implant through the vaginal incision; placing the mesh support portion in a position superior to vaginal tissue, to support a bladder; making a superior left external incision at an inner thigh adjacent to a left obturator foramen, preparing a tissue path between the superior left external incision and the lateral vaginal tissue on a left side of the vagina, passing an extension portion through the tissue path between the superior left external incision and the lateral vaginal tissue on the left side of the vagina; making an inferior left external incision at an inner thigh adjacent to a left obturator foramen, preparing a tissue path between the inferior left external incision and the lateral vaginal tissue on a left side of the vagina, passing an extension portion through the tissue path between the inferior left external incision and the lateral vaginal tissue on the left side of the vagina; making a superior right external incision at an inner thigh adjacent to a right obturator foramen, preparing a tissue path between the superior right external incision and the lateral vaginal tissue on a right side of the vagina, passing an extension portion through the tissue path between the superior right external incision and the lateral vaginal tissue on the right side of the vagina; making an inferior right external incision at an inner thigh adjacent to a right obturator foramen, preparing a tissue path between the inferior right external incision and the lateral vaginal tissue on a right side of the vagina, and passing an extension portion through the tissue path between the inferior right external incision and the lateral vaginal tissue on the right side of the vagina.

In another aspect, the invention relates to a method of treating cystocele, including treating a lateral vaginal defect. The method includes: providing a system of implants as described; making an upper vaginal midline incision; passing a first implant of the system through the vaginal incision; placing a mesh support portion of the first implant in contact with lateral vaginal tissue on a left side of the vagina; making a superior left external incision at an inner thigh adjacent to a left obturator foramen, preparing a tissue path between the superior left external incision and the lateral vaginal tissue on a left side of the vagina, passing a first extension portion of the first implant through the tissue path between the superior left external incision and the lateral vaginal tissue on the left side of the vagina; making an inferior left external incision at an inner thigh adjacent to a left obturator foramen, preparing a tissue path between the inferior left external incision and the lateral vaginal tissue on a left side of the vagina, passing a second extension portion of the first implant through the tissue path between the inferior left external incision and the lateral vaginal tissue on the left side of the vagina; passing a second implant through the vaginal incision; placing a mesh support portion of the second implant in contact with lateral vaginal tissue on a right side of the vagina; making a superior right external incision at an inner thigh adjacent to a right obturator foramen, preparing a tissue path between the superior right external incision and the lateral vaginal tissue on a right side of the vagina, passing a first extension portion of the second implant through the tissue path between the superior right external incision and the lateral vaginal tissue on the right side of the vaginal; making an inferior right external incision at an inner thigh adjacent to a right obturator foramen, preparing a tissue path between the inferior right external incision and the lateral vaginal tissue on a right side of the vagina, and passing a second extension portion of the second implant through the tissue path between the inferior right external incision and the lateral vaginal tissue on the right side of the vagina.

BRIEF DESCRIPTION OF THE DRAWINGS

FIG. 2 illustrates a system or kit as described, including two implants.

FIGS. 3A and 3B illustrate examples of needles useful according to methods described herein.

DETAILED DESCRIPTION

Figure 1A:
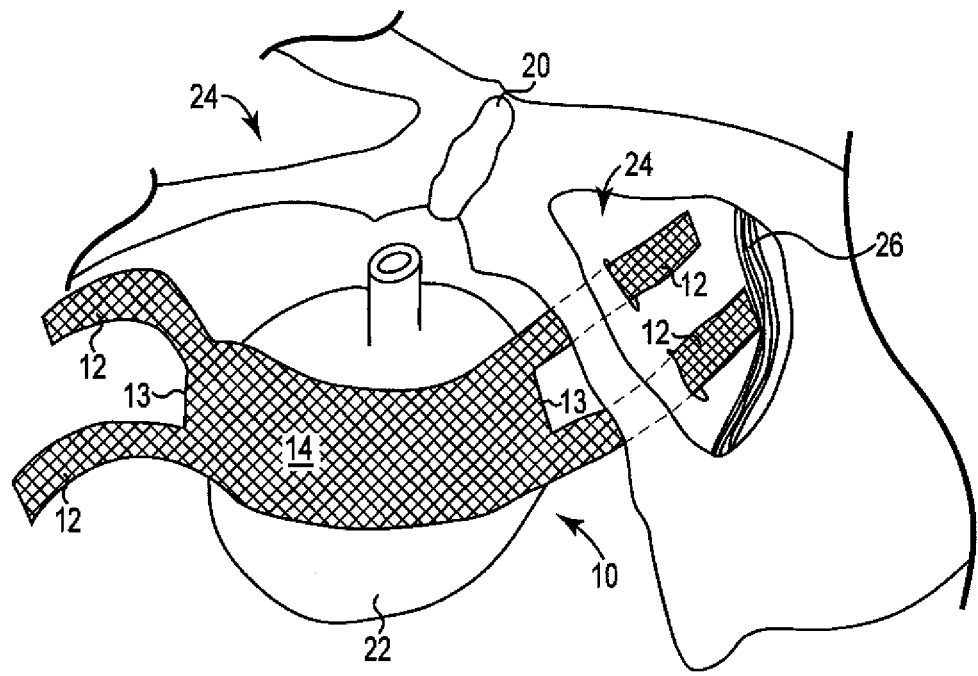
FIG. 1A is a perspective view of an embodiment of an implant as described, at least partially implanted in an illustrated pelvis.

The inventive concept utilizes the transobturator approach (used successfully by AMS for suburethral slings) and has two designs concepts. One design or embodiment is the TARS or TAWS (Total anterior vaginal reconstruction system, or Total Anterior Wall Shelf) (see FIG. 1A). The other design or embodiment is the PARS (Para vaginal Anterior vaginal reconstruction) see FIG. 4.

An implant can generally include a support portion that contacts tissue to be supported, and two or more opposing extension portions that extend away from the support portion. The terms "support portion" and "extension portion" can be used specifically or generally to denote precise or general portions of an implant. When an implant has a uniform shape from end to end, as does a simple mesh strip, the end portions will not necessarily exhibit a distinct boundary relative to the support portion.

Exemplary implants may be in the form of a continuous mesh tape that includes a support portion located at the center of the mesh, and two end portions, one end portion extending in each direction from the central support portion. Other implants can include a support portion having larger dimensions relative to the extension portions, with multiple (e.g., two or four) elongate extension portions extending from the support portion.

In one embodiment, a size and shape of an implant support portion can be for use to contact and support vaginal tissue, nearby bladder tissue, or both, to treat prolapse, specifically anterior defects, lateral defects, and cystocele. These exemplary implants may be useful in the TARS and TAWS procedures. For example, a support portion may be sized to contact and support a bladder superior to prolapsed vaginal tissue. Functionally, such a support portion may be designed to act as support for the bladder, as a replacement to, or reinforcement of, the hammock-type tissue that naturally supports the bladder, including pubocervical fascia. The support portion can be placed to contact bladder tissue and tissue supportive of the bladder, including pubocervical fascia. The support portion can be attached to the bladder support tissue (e.g., pubocervical fascia) and may extend to be near (within 1 centimeter from) or in contact with the arcus tendineus. Such embodiments of support portions can include curved or circular edges and may be circular in shape (meaning circular, oblong, oval, or approximately circular with multiple obtuse angles). Alternate support portions may be square, rectangular, or rectangular with rounded ends, such as rectangular with rounded anterior and posterior ends. A support portion may be of a size to extend from one lateral side of a pelvic region, below a bladder, and across to the other lateral side of the pelvic region, e.g., from near or in contact with one arcus tendineus, across the pelvic region and below a bladder, to a position that is near or in contact with an opposing arcus tendineus. The mesh support portion can form new support tissue for the bladder (e.g., a hammock) over which the bladder is suspended.

Other implant embodiments, e.g., useful in the PARS and PAWS embodiments, can include a support portion that can be connected to lateral vaginal tissue (vaginal sulcus) on one side of a vagina. Two of these implants can be used in combination, one being implanted on each of a left side and a right side of a vagina, to support both a lateral left side and a lateral right side tissue of a vagina, to treat paravaginal, lateral, and anterior defects and cystocele. For example, such a support portion can be in the form of an elongate strip having a length in the range from about 4 to about 5 centimeters and width in the range from about 0.5 to about 1.3 centimeters.

Optionally and preferably an implant can include one or more appurtenant features including a tensioning device (or "tensioning member") such as a suture or a sheath, and a connector or a dilating connector (e.g., "dilator," suture, or the like) that removably or securely (e.g., permanently) engages a tip of a needle of an implantation tool.

In various embodiments an implant may be a one piece mesh strip with the support portion substantially continuous with (i.e., integral with) end portions, also optionally including a plastic sheath enclosing the mesh strip, an optional tensioning suture running along all or a portion of the length of the mesh strip, and one or two connectors, sutures, or dilators, one at the end of each extension portion. Yet a further feature can be one or more sutures or other attachment mechanisms located and attached at an end of the implant or along a length of the implant, for example extending from a support portion or an extension portion.

An implant can be placed within a tissue path by assistance of an insertion tool. Examples of insertions tool that include an elongate needle useful to prepare one or more of the tissue paths described herein, include those described at United States Patent Applications 2005/0245787 (Ser. No. 10/834, 943), 2007/0068538 (Ser. No. 11/518,932), 2005/0143618 (Ser. No. 11/064,875), and 2009-0023978 (Ser. No. 12/229, 655), the entireties of these documents being incorporated herein by reference. Such tools generally include a handle and an elongate needle portion that is curved in two or three dimensions. The needle can be used to create a tissue path extending from an external incision to a region of vaginal tissue near a vaginal (e.g., mid-line) incision, and also to pull or push an implant or a portion thereof (e.g., extension portion) through the tissue path.

Referring to the example embodiment of TARS and TAWS illustrated at FIGS. 1A through 1E, embodiments of these implant can have varied shapes and configurations. In at least one embodiment of each there can be a central portion (or "support portion") capable of supporting an anatomical structure such as the bladder. A number of arms (or "extension portions") useful to secure the implant in a patient can extend away from the support portion.

Referring specifically to FIG. 1A, this illustration shows a pelvic region including pelvic bone, pubic symphasis 20, right and left obturator foramen 24, bladder 22, and obturator vessels and nerves 26. Implant 10 includes mesh support portion 14 positioned above a vagina (not shown) to support the bladder. The implant can be positioned in a manner to support bladder 22 and treat cystocele, e.g., due to a lateral, e.g., paravaginal defect. The positioning can include placing support portion 14 below bladder 22, optionally with edges 13 located near or in contact with tissue of opposing arcus tendineus (not shown), e.g., each edge 13 can be located within 1 centimeter of a right or left arcus tendineus, or in contact with the arcus tendineus.

Still referring to FIG. 1, four longitudinal extension portions 12 extend away from support portion 14. Each extension portion 12 extends within a tissue path leading from a region of the vaginal tissue to an obturator foramen. (Two extension portions 12 are shown in implanted positions through an obturator foramen, and two others are shown partially implanted.) Two superior (anterior) arms (alternately considered, an anterior segment or edge of the support portion) can be placed at or just below the bladder neck and extend to a superior incision. Two inferior (posterior) arms (alternately considered, a posterior segment or edge of the support portion) can be placed 1.5 centimeters proximal to the ischial spine. Each extension portion can be extended through an obturator foramen at a separate incision, one superior and one inferior, and then continue further through an external incision (not shown), including one superior external incision and one inferior external incision per side of the patient. An example of a superior external incision may be placed approximately 0.5 centimeters medial to a geniot crural fold at the level of the clitoris below an adductor longus tendon. An example of an inferior external incision may be placed approximately 2 centimeters lateral to and 3 centimeters below the superior incision; this point should correspond to the lowermost portion of the obturator membrane directly above the ischial tuberosity—if by palpation this point is askew then the palpatory point can be used for precise incision inferiorly.

Figure 1B:
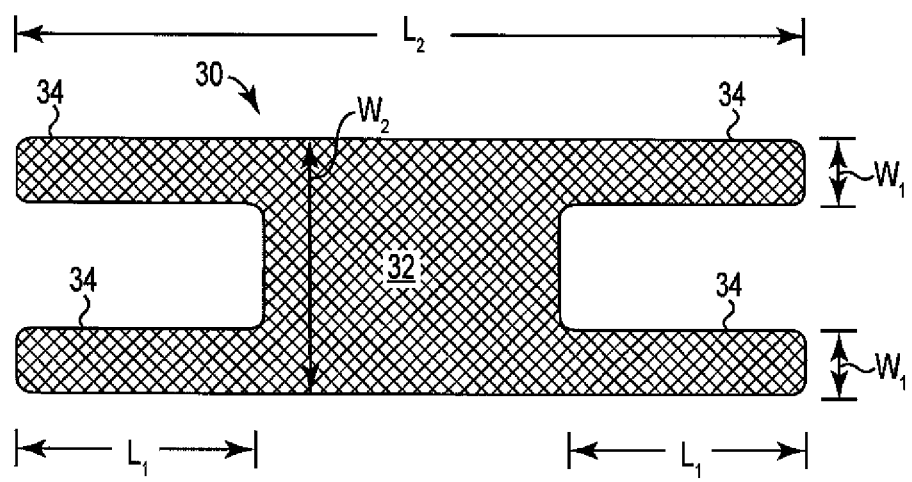
FIGS. 1B-1E are various configurations of implants as described.

FIG. 1B shows a specific design of a mesh implant useful according to the TARS embodiment, e.g., as illustrated at FIG. 1A. Implant 30 includes rectangular or square support portion 32 and four elongate extension portions 34, each extending away from a corner of support portion 32. Length dimension L2, the length of the total implant including support portion 32 and two opposing extension portions 34, may be from 15 to 20 centimeters. Lengths L1 of each extension portion 34 may be, e.g., from 4 to 6 centimeters. Width W2 of support portion 32 can be, e.g., from 3 to 6 centimeters. Width W1 of each extension portion 32 can be from 0.5 to 1.3 centimeter.

Figure 1C:
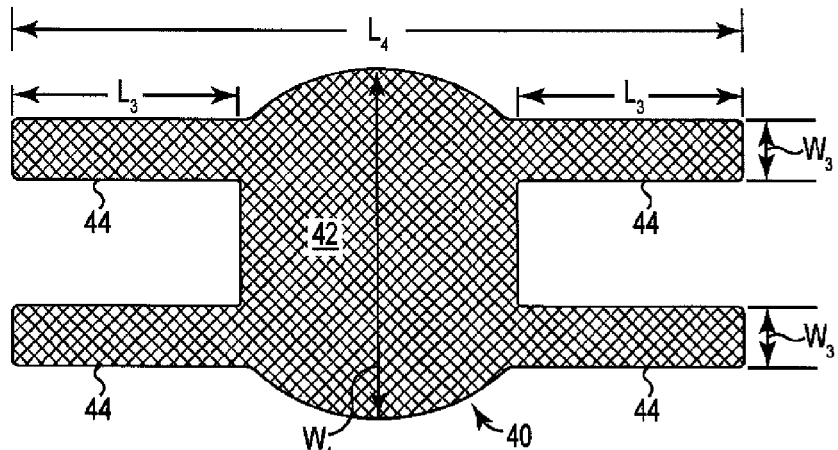

FIG. 1C shows another specific design of a mesh implant useful according to the TARS embodiment, e.g., as illustrated at FIG. 1A. Implant 40 includes support portion 42 and four elongate extension portions 44, each extending away from a corner of support portion 42. Support portion 42 is rectangular with rounded anterior and posterior ends. Length dimension L4 may be from 15 to 20 centimeters. Lengths L3 of each extension portion 44 may be, e.g., from 4 to 6 centimeters. Width W4 of support portion 42, including the two rounded ends can be, e.g., from 3 to 8 centimeters. Width W3 of each extension portion 4 can be from 0.5 to 1.3 centimeter.

Figure 1D:
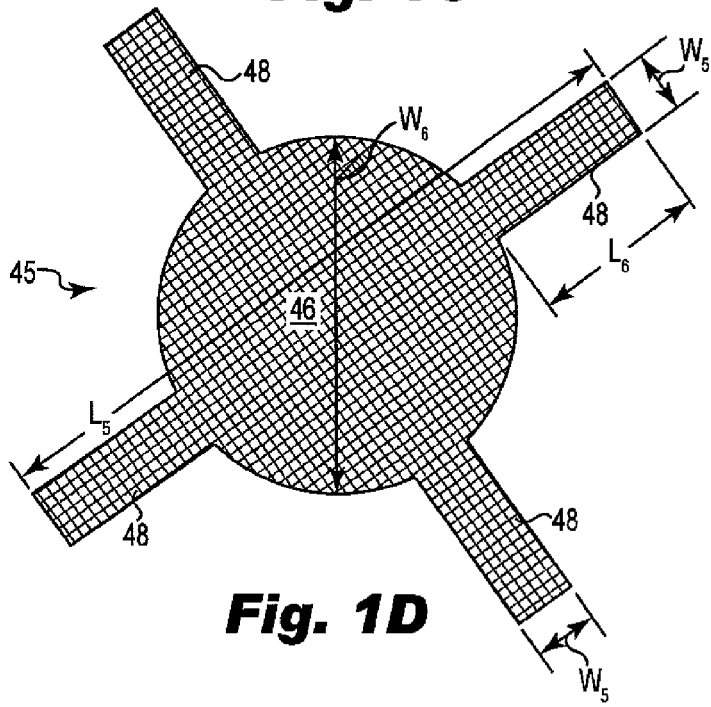

FIG. 1D shows another specific design of a mesh implant useful according to the TARS embodiment, e.g., as illustrated at FIG. 1A. Implant 45 includes support portion 46 and four elongate extension portions 48. Each extension portion extends away from an edge (e.g., corner) of support portion 46 in a direction perpendicular to the edge of the circular support portion. Alternately, other angles may be useful; for example extension portions 48 of implant 45 may be arranged similarly to extension portions 44 of implant 40, sets of extension portions extending from the support portion in parallel and opposing directions. Support portion 46 is circular and may be oval or oblong. Length dimension L5 may be from 15 to 20 centimeters. Lengths L6 of each extension portion 48 may be, e.g., from 4 to 6 centimeters. Width (diameter) W6 of support portion 46 can be, e.g., from 3 to 8 centimeters. Width W5 of each extension portion 48 can be from 0.5 to 1.3 centimeter.

Figure 1E:
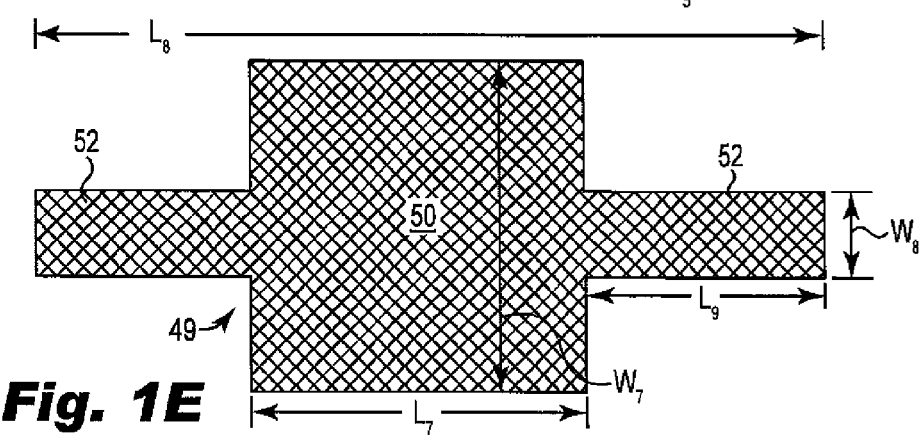

FIG. 1E shows another specific design of a mesh implant useful according to the TARS embodiment, e.g., as illustrated at FIG. 1A. Implant 49 includes support portion 50 and two elongate extension portions 52. Each extension portion extends away from an edge of support portion 50 in a direction perpendicular to the edge, and opposite and parallel with the opposing extension portion. Support portion 50 is square but may be rectangular, trapezoidal, etc. Length dimension L8 may be from 15 to 20 centimeters. Lengths L9 of each extension portion 52 may be, e.g., from 4 to 6 centimeters. Width W7 of support portion 50 can be, e.g., from 3 to 6 centimeters. Length L9 of support portion 50 can be, e.g., from 3 to 6 centimeters. Width W8 of each extension portion 52 can be from 0.5 to 1.3 centimeter.

Referring to an embodiment of a system of implants useful in the PARS method, illustrated in FIG. 2, each of a pair of implants can be a generally elongate member having a pair of ends, i.e., mesh strips of substantially uniform length and construction. Implants 60 and 62 each include a mesh support portion ($P_S$) (preferably from 4 to 6 centimeters in length and from 0.5 to 1.3 centimeters wide) and two extension portions ($P_E$), one on either side of the support portion (also preferably from 4 to 6 centimeters in length and from 0.5 to 1.3 centimeters wide). A guide suture or other guide device can be attached to each end of the mesh strip; as illustrated, sutures 64 are attached at each end of implants 60 and 62. The guide sutures on the ends of the elongate body can be used to pull the elongate member through a tissue path, e.g., by assistance using an insertion tool, optionally a two dimensional or a helical insertion tool. For example guide sutures 64 can be attached to needles, illustrated in FIGS. 3A and 3B, which can be used to guide and pull the elongate member through the patient's tissue.

As particularly illustrated in FIG. 2, placement sutures or anchors can be disposed on a portion of the elongate member between its ends, along its length. As illustrated, three placement sutures 66 are located along the length of the implant and can be used to position or place the elongate member on an anatomical structure such as the vaginal sulcus, e.g., the sutures can be attached to vaginal tissue such as vaginal sulcus tissue.

Implant 62 of FIG. 2 includes an optional sheath 68, covering the support portion, placement sutures 66, and at least portions of extension portions. The sheath can be a transparent plastic sheath or envelope, for example, that can remain on the sheath during insertion and that can be removed after the position of the implant is adjusted as desired.

Implants 60 and 62 can be made from any material such as a mesh material and the placement sutures and guide sutures can be made from any material such as the material used for vicryl sutures. As illustrated in FIG. 2, the elongate member can be enclosed by a plastic sheath or envelope that aids in moving the elongate member through a patient's tissue. The sheath or envelope can be made of any material such as plastic or paper, optionally lubricated, and can preferably be a clear flexible plastic.

Figure 4:
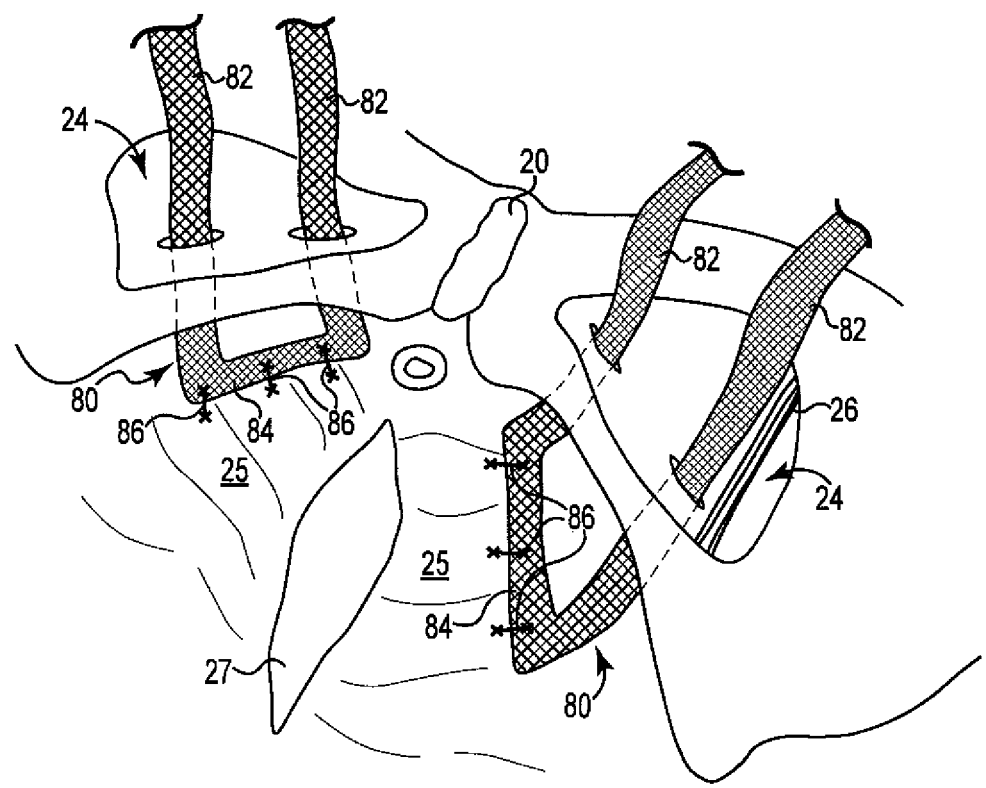
FIG. 4 is a perspective view of an embodiment of a system of implants as described.

FIG. 4 illustrates a pelvic region including pelvic bone, pubic symphasis 20, right and left obturator foramen 24, vaginal sulci 25, midline incision 27 in vaginal tissue, and obturator vessels and nerves 26. Each implant 80 is a mesh strip that includes mesh support portion 84, extension portions 82, and sutures 86. Each mesh support portion 84 is attached to lateral vaginal tissue (sulcus) by sutures 86. Each extension portion 82 extends within a tissue path leading from a region of vaginal tissue to an obturator foramen. As illustrated, each extension portion 82 further extends through the obturator foramen at a separate incision (one incision for each extension portion 82), one superior and one inferior, and then continues further through an external incision (not shown), including one superior external incision and one inferior external incision, per side of the patient.

Referring to FIGS. 3A and 3B, insertion tool 70 comprising needle 72 and handle 74 is suitable for use in methods described herein. Handle 72 can be any suitable handle known in the art or otherwise useful. U.S. Pat. No. 6,652,450, hereby incorporated by reference in its entirety, discloses several possible configurations. Needle 72 is generally curved or arcuate, preferably in three dimensions, to form a helix as illustrated. The shape of needle 72 should facilitate and provide controlled passage of needle 74 through tissue as required, e.g., to allow the tip to pass from an external incision at a labia or inner groin region of a patient, through an obturator foramen, and to a region of vaginal tissue.

End or tip 76 of needle 72 can be configured to engage an end of an implant, such as a dilator, connector, suture, or mesh piece at an end of an implant. Many different configurations of such a system are known and within the scope of the present invention. Several are disclosed in U.S. Pat. No. 6,652,450, which is incorporated by reference, as well as other patent documents identified herein. Tip 76 is generally not sharpened but may be tapered to afford easy passage through tissue while providing a blunt surface that avoids cutting sensitive tissue. It is preferred that the diameter of needle 72 be small, to reduce tissue trauma.

To perform a TARS or TAWS placement, the patient is placed in a lithotomy position. The physician makes a midline vaginal incision and dissects equal to a typical central cystocele repair. External incisions are then made near the obturator foramen, e.g., a superior external incision and an inferior external incision, one on each side of the patient. Using a two- or three-dimensionally curved needle, such as the one illustrated in FIGS. 3A and 3B, an end of the needle can be pushed through an external incision and through the obturator foramen to enter the vagina through the vaginal incision, to meet and engage an extension portion of the implant. A second needle (two-dimensionally or three-dimensionally curved) can be used in a second incision through the obturator foramen. One of the needles can enter into a lower ⅓ of the vagina and the other needle can enter into a mid portion of the vagina. The arms (extension portions) of the implant can be attached to the needles, which can be withdrawn through the obturator foramen. Anterior (superior) extension portions or an anterior edge or portion of the implant can be placed under the base of the bladder or 1 cm inferior to the base of the bladder or just below the bladder neck. Inferior (posterior) extension portions or a posterior edge or portion of the implant can be placed at the vagina approximately 1 centimeter proximal to the ischial spine.

Exemplary steps of a method of placing an implant as illustrated at FIG. 1, for treating a lateral vaginal defect (e.g., paravaginal defect) and related cystocele, can include the following features.

Providing an implant as described, having a support portion and four extension portions.

Making an upper vaginal midline incision.

Passing the implant through the vaginal incision.

Placing the mesh support portion in a position superior to vaginal tissue, to support a bladder. The mesh support portion may extend below the bladder, optionally to opposing arcus tendineus of the patient, either to contact the arcus tendineus or to be within 1 centimeter of the arcus tendineus. The mesh support portion may optionally be attached, e.g., by suture, staple, or other securement mechanism, to tissue such as pubocervical fascia, arcus tendineus, or both.

Making a superior left external incision at an inner thigh adjacent to a left obturator foramen.

Preparing a tissue path between the superior left external incision and the lateral vaginal tissue on a left side of the vagina, e.g., using a helical needle.

Passing an extension portion through the tissue path between the superior left external incision and the lateral vaginal tissue on the left side of the vagina.

Making an inferior left external incision at an inner thigh adjacent to a left obturator foramen.

Preparing a tissue path between the inferior left external incision and the lateral vaginal tissue on a left side of the vagina, e.g., using a helical needle.

Passing an extension portion through the tissue path between the inferior left external incision and the lateral vaginal tissue on the left side of the vagina.

Making a superior right external incision at an inner thigh adjacent to a right obturator foramen, Preparing a tissue path between the superior right external incision and the lateral vaginal tissue on a right side of the vagina, e.g., using a helical needle.

Passing an extension portion through the tissue path between the superior right external incision and the lateral vaginal tissue on the right side of the vagina.

Making an inferior right external incision at an inner thigh adjacent to a right obturator foramen, Preparing a tissue path between the inferior right external incision and the lateral vaginal tissue on a right side of the vagina, e.g., using a helical needle.

And passing an extension portion through the tissue path between the inferior right external incision and the lateral vaginal tissue on the right side of the vagina.

To perform a PARS placement, a physician identifies a defect such as displacement cystocele with paravaginal defect. The physician can then clearly identify the vaginal sulcus and ensure there is sufficient tissue to attach implant material on both sides if necessary. A surgical marker can be used if needed. A mid-line vaginal incision can be made and routine para urethral dissection into the retropubic space is conducted. Next, a digital palpitation of posterior aspect of obturator internus is done. A physician should then palpate on the external skin of vulva where the mesh will pull through in 2 points (e.g., a superior incision and an inferior incision as these are described herein). The mesh (support portion) can then be attached to the vaginal sulcus with the placement sutures. Additional placement sutures can be trimmed or attached if necessary.

An external incision can be made near the obturator foreman. Using a needle such as the one illustrated in FIGS. 3A and 3B, its end can be pushed through the obturator foramen to enter the vagina through the midline incision. Repeat at a posterior-inferior site keeping clear of the obturator vessels. To ensure proper placement, the ends of the needles can be guided using one or more digits of your hand within the retropubic space.

In one embodiment, the guide sutures can be attached to the needles and the mesh (mesh strip implant) can be pulled through the obturator foramen and external incision. While pulling the mesh placement should be checked on both sides without removing the plastic sheath (if present). Ensure that the midline vaginal incision can be closed without tension. The vaginal incision is then closed and the midline fascia can be repaired if necessary. The implant can then be adjusted. Lastly, the plastic envelope (if present) can be removed and the mesh implant can be trimmed flush with the skin. The mesh implant can be left unsutured or sutured.

Exemplary steps of a method of placing a system of implants as illustrated at FIG. 3, for treating a paravaginal defect and related cystocele, can include the following features.

Providing a system of implants as described herein, e.g., as illustrated at FIG. 3.

Making an upper vaginal midline incision.

Passing a first implant through the vaginal incision.

Placing a mesh support portion of the first implant in contact with lateral vaginal tissue (sulcus) on a left side of the vagina.

Making a superior left external incision at an inner thigh adjacent to a left obturator foramen.

Preparing a tissue path between the superior left external incision and the lateral vaginal tissue (sulcus) on a left side of the vagina, Passing a superior extension portion of the first implant through the tissue path between the superior left external incision and the lateral vaginal tissue on the left side of the vagina.

Making an inferior left external incision at an inner thigh adjacent to a left obturator foramen.

Preparing a tissue path between the inferior left external incision and the lateral vaginal tissue on a left side of the vagina, Passing an inferior extension portion of the first implant through the tissue path between the inferior left external incision and the lateral vaginal tissue on the left side of the vagina.

Passing a second implant through the vaginal incision.

Placing a mesh support portion of the second implant in contact with lateral vaginal tissue (sulcus) on a right side of the vagina.

Making a superior right external incision at an inner thigh adjacent to a right obturator foramen.

Preparing a tissue path between the superior right external incision and the lateral vaginal tissue on a right side of the vagina.

Passing a superior extension portion of the second implant through the tissue path between the superior right external incision and the lateral vaginal tissue on the right side of the vagina.

Making an inferior right external incision at an inner thigh adjacent to a right obturator foramen.

Preparing a tissue path between the inferior right external incision and the lateral vaginal tissue on a right side of the vagina.

And passing an inferior extension portion of the second implant through the tissue path between the inferior right external incision and the lateral vaginal tissue on the right side of the vagina.

The invention claimed is:

1. A method of treating cystocele with a system comprising first and second implants, each implant comprising a mesh support portion and two mesh extension portions, wherein the mesh support portion of each implant is configured for contacting vaginal sulcus tissue while the two mesh extension portions extend to tissue of an obturator foramen, the method comprising:

making an upper vaginal midline incision;
  passing the first implant through the vaginal incision;
  placing the mesh support portion of the first implant in contact with lateral vaginal tissue on a left side of the vagina;
  making a superior left external incision at an inner thigh adjacent to a left obturator foramen;
  preparing a tissue path between the superior left external incision and the lateral vaginal tissue on the left side of the vagina;
  passing a first mesh extension portion of the first implant through the tissue path between the superior left external incision and the lateral vaginal tissue on the left side of the vagina;
  making an inferior left external incision at the inner thigh adjacent to the left obturator foramen;
  preparing a tissue path between the inferior left external incision and the lateral vaginal tissue on the left side of the vagina;
  passing a second mesh extension portion of the first implant through the tissue path between the inferior left external incision and the lateral vaginal tissue on the left side of the vagina;
  passing the second implant through the vaginal incision;
  placing the mesh support portion of the second implant in contact with lateral vaginal tissue on a right side of the vagina;
  making a superior right external incision at the inner thigh adjacent to a right obturator foramen;
  preparing a tissue path between the superior right external incision and the lateral vaginal tissue on the right side of the vagina;
  passing a third mesh extension portion of the second implant through the tissue path between the superior right external incision and the lateral vaginal tissue on the right side of the vagina;
  making an inferior right external incision at the inner thigh adjacent to the right obturator foramen;
  preparing a tissue path between the inferior right external incision and the lateral vaginal tissue on the right side of the vagina; and
  passing a fourth mesh extension portion of the second implant through the tissue path between the inferior right external incision and the lateral vaginal tissue on the right side of the vagina.

2. The method of claim 1;
  wherein the first implant comprises a first mesh support portion having a length that corresponds with a distance between a superior incision and an inferior incision through a first obturator foramen, and the first and second mesh extension portions extend from opposite ends of the first mesh support portion, wherein each of the first and second mesh extension portions has a longitudinal axis that is at an angle greater than zero relative to a longitudinal axis of the first mesh support portion;

wherein the second implant comprises a second mesh support portion having a length that corresponds with a distance between a superior incision and an inferior incision through a second obturator foramen, and the third and fourth mesh extension portions extend from opposite ends of the second mesh support portion, wherein each of the third and fourth mesh extension portions has a longitudinal axis that is at an angle greater than zero relative to a longitudinal axis of the second mesh support portion; and wherein the first and second mesh support portions of the first and second implants are sized for contacting vaginal sulcus tissue while the two extension portions of each of the first and second implants extend to the superior and inferior incisions of the first and second obturator foramen, respectively.

3. The method of claim 1, further comprising at least one placement suture attached to the first mesh support portion and at least one placement suture attached to the second mesh support portion, wherein each of the placement sutures is attachable to vaginal sulcus tissue.

4. The method of claim 1 wherein each implant comprises a mesh strip, each support portion has a length of from 4 to 6 centimeters, the total length of each mesh strip is from 15 to 20 centimeters, and the width of each mesh strip is in the range from 0.5 to 1.3 centimeters.

5. The method of claim 1 comprising one or multiple helical needles.

6. The method of claim 1 wherein each of the first and second implants comprises two sutures, one suture connected at each opposing end of the respective implant.

7. The method of claim 1 wherein each of the first and second implants comprises one or multiple sutures connected along a length of the implant.

8. The method of claim 1 wherein each of the first and second implants comprises a sheath that covers the support portion and at least portions of the extension portions.

* * * * *